US008853377B2

(12) United States Patent  (10) Patent No.: US 8,853,377 B2
Guild et al.  (45) Date of Patent: Oct. 7, 2014

(54) MRNA FOR USE IN TREATMENT OF HUMAN GENETIC DISEASES

(75) Inventors: Braydon Charles Guild, Concord, MA (US); Michael Heartlein, Boxborough, MA (US)

(73) Assignee: Shire Human Genetic Therapies, Inc., Lexington, MA (US)

(*) Notice: Subject to any disclaimer, the term of this patent is extended or adjusted under 35 U.S.C. 154(b) by 0 days.

(21) Appl. No.: 13/306,781

(22) Filed: Nov. 29, 2011

(65) Prior Publication Data

US 2012/0142756 A1  Jun. 7, 2012

Related U.S. Application Data

(60) Provisional application No. 61/418,389, filed on Nov. 30, 2010.

(51) Int. Cl.
C07H 21/02 (2006.01)
A61K 9/127 (2006.01)

(52) U.S. Cl.
USPC ..... 536/23.1; 536/23.2; 536/23.5; 536/23.51; 536/24.1; 424/450

(58) Field of Classification Search
CPC . A61K 48/00; A61K 2300/00; A61K 38/215; A61K 38/217; A61K 31/00; A61K 38/00; A61K 31/711; C12N 2310/321; C12N 2310/3521; C12N 15/113; C12Q 1/6886
See application file for complete search history.

(56) References Cited

U.S. PATENT DOCUMENTS

| 4,737,323 | A | 4/1988 | Martin et al. |
| 4,920,016 | A | 4/1990 | Allen et al. |
| 4,946,683 | A | 8/1990 | Forssen |
| 5,194,654 | A | 3/1993 | Hostetler et al. |
| 5,223,263 | A | 6/1993 | Hostetler et al. |
| 5,279,833 | A | 1/1994 | Rose |
| 5,677,124 | A | 10/1997 | DuBois et al. |
| 5,744,335 | A | 4/1998 | Wolff et al. |
| 5,783,383 | A * | 7/1998 | Kondo et al. ..................... 435/5 |
| 5,885,613 | A | 3/1999 | Holland et al. |
| 6,147,055 | A | 11/2000 | Hobart et al. |
| 6,165,763 | A | 12/2000 | Brown et al. |
| 6,271,208 | B1 | 8/2001 | Bischoff |
| 6,287,951 | B1 | 9/2001 | Lucas et al. |
| 6,417,326 | B1 | 7/2002 | Cullis et al. |
| 6,534,484 | B1 | 3/2003 | Wheeler et al. |
| 6,586,410 | B1 | 7/2003 | Wheeler et al. |
| 6,670,178 | B1 | 12/2003 | Selden et al. |
| 6,733,777 | B2 | 5/2004 | Erbacher et al. |
| 6,743,823 | B1 | 6/2004 | Summar et al. |
| 6,790,838 | B2 * | 9/2004 | Alison et al. ................ 514/44 R |
| 6,815,432 | B2 | 11/2004 | Wheeler et al. |
| 6,835,395 | B1 | 12/2004 | Semple et al. |
| 6,858,224 | B2 | 2/2005 | Wheeler et al. |
| 6,858,225 | B2 | 2/2005 | Semple et al. |
| 7,067,697 | B2 | 6/2006 | Gao |
| 7,341,738 | B2 | 3/2008 | Semple et al. |
| 8,021,686 | B2 | 9/2011 | Semple et al. |
| 2003/0083272 | A1 | 5/2003 | Wiederholt et al. |
| 2004/0110709 | A1 | 6/2004 | Li et al. |
| 2005/0032730 | A1 | 2/2005 | Von Der Mulbe et al. |
| 2005/0054026 | A1 | 3/2005 | Atsushi et al. |
| 2005/0059624 | A1 | 3/2005 | Hoerr et al. |
| 2005/0065107 | A1 * | 3/2005 | Hobart et al. .................... 514/44 |
| 2005/0250723 | A1 | 11/2005 | Hoerr et al. |
| 2006/0008910 | A1 | 1/2006 | MacLachlan et al. |
| 2006/0083780 | A1 | 4/2006 | Heyes et al. |
| 2006/0172003 | A1 | 8/2006 | Meers et al. |
| 2006/0204566 | A1 | 9/2006 | Smyth-Templeton et al. |
| 2007/0252295 | A1 | 11/2007 | Panzner et al. |
| 2007/0281336 | A1 | 12/2007 | Jendrisak et al. |
| 2008/0260706 | A1 | 10/2008 | Rabinovich et al. |
| 2009/0093433 | A1 | 4/2009 | Woolf et al. |
| 2009/0186805 | A1 | 7/2009 | Tabor et al. |
| 2009/0221684 | A1 | 9/2009 | Grinstaff et al. |
| 2010/0028943 | A1 | 2/2010 | Thomas et al. |
| 2010/0047261 | A1 | 2/2010 | Hoerr et al. |
| 2010/0189729 | A1 | 7/2010 | Hoerr et al. |
| 2010/0267806 | A1 | 10/2010 | Bumcrot et al. |
| 2011/0038941 | A1 | 2/2011 | Lee et al. |
| 2011/0244026 | A1 | 10/2011 | Guild et al. |
| 2012/0065252 | A1 | 3/2012 | Schrum et al. |
| 2012/0195936 | A1 | 8/2012 | Rudolph et al. |
| 2012/0237975 | A1 | 9/2012 | Schrum et al. |
| 2012/0251618 | A1 | 10/2012 | Schrum et al. |

FOREIGN PATENT DOCUMENTS

| CA | 2807552 A1 | 2/2012 |
| WO | WO-96/37211 A1 | 11/1996 |
| WO | WO-02/34236 A2 | 5/2002 |
| WO | WO-2005/037226 A2 | 4/2005 |
| WO | WO-2007/024708 A2 | 3/2007 |

(Continued)

OTHER PUBLICATIONS

U.S. Appl. No. 60/083,294, Apr. 28, 1998, Chen et al.
Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-2025 (2003).
Bloomfield, V.A., Quasi-Elastic Light Scattering Applications in Biochemistry and Biology, Ann. Rev. Biophys. Bioeng. 10:421-450 (1981).
Caplen, N.J. et al., In vitro liposome-mediated DNA transfection of epithelial cell lines using the cationic liposome DC-Chol/DOPE, Gene Therapy, 2:603-613 (1995).
Cowling, V.H., Regulation of mRNA cap methylation, Biochemical Journal, 425:295-302 (2010).

(Continued)

Primary Examiner — Richard Schnizer
(74) Attorney, Agent, or Firm — Choate, Hall & Stewart LLP; Fangli Chen

(57) ABSTRACT

Compositions for modulating the expression of a protein in a target cell comprising at least one RNA molecule which comprises at least one modification conferring stability to the RNA, as well as related methods, are disclosed.

14 Claims, 1 Drawing Sheet

(56) References Cited

FOREIGN PATENT DOCUMENTS

| | | |
|---|---|---|
| WO | WO-2007/126386 A1 | 11/2007 |
| WO | WO-2008/083949 A2 | 7/2008 |
| WO | WO-2009/127060 A1 | 10/2009 |
| WO | WO-2009/127230 A1 | 10/2009 |
| WO | WO-2010/054401 A1 | 5/2010 |
| WO | WO-2010/054405 A1 | 5/2010 |
| WO | WO-2010/119256 A1 | 10/2010 |
| WO | WO-2010/144740 A1 | 12/2010 |
| WO | WO 2011/068810 | 6/2011 |
| WO | WO-2012/019168 A2 | 2/2012 |
| WO | WO-2012/019630 A1 | 2/2012 |
| WO | WO-2012/019780 A1 | 2/2012 |
| WO | WO-2012/045075 A1 | 4/2012 |
| WO | WO-2012/045082 A2 | 4/2012 |
| WO | WO-2012/135805 A2 | 10/2012 |
| WO | WO-2013/039857 A1 | 3/2013 |
| WO | WO-2013/039861 A2 | 3/2013 |

OTHER PUBLICATIONS

Drummond, D.C. et al., Optimizing Liposomes for Delivery of Chemotherapeutic Agents to Solid Tumors, Pharmacological Reviews, 51(4): 691-743 (1999).

Fechter, P. et al., Recognition of mRNA cap structures by viral and cellular proteins, Journal of General Virology, 86:1239-1249 (2005).

Gao, X. et al., A novel cationic liposome reagent for efficient transfection of mammalian cells, Biochemical and Biophysical Research Communications, 179(1):280-285 (1991).

Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).

Gordon, N. Ornithine transcarbamylase deficiency: a urea cycle defect, European Journal of Paediatric Neurology, 7:115-121 (2003).

Guttman, M. et al., Chromatin signature reveals over a thousand highly conserved large non-coding RNAs in mammals, Nature, 458:223-227 (2009).

Hata, A. et al., Isolation and Characterization of the Human Ornithine Transcarbamylase Gene: Structure of the 5'-End Region, Journal of Biochemistry, 100:717-725 (1986).

Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).

Higman, M.A. et al., The mRNA (Guanine-7-)methyltransferase Domain of the Vaccinia Virus mRNA Capping Enzyme, The Journal of Biological Chemistry, 269(21):14974-14981 (1994).

Hillery, A.M. et al., Drug Delivery and Targeting for Pharmacists and Pharmaceutical Scientists, Taylor and Francis (2005).

Hope, M.J. et al., Reduction of Liposome Size and Preparation of Unilamellar Vesicles by Extrusion Techniques, In: Liposome Technology, 1:123-139 (1993).

Horwich, A.L. et al., Structure and Expression of a Complementary DNA for the Nuclear Coded Precursor of Human Mitochondrial Ornithine Transcarbamylase, Science, 224(4653):1068-1074 (1984).

Horwich, A.L. et al., Targeting of Pre-Ornithine Transcarbamylase to Mitochondria: Definition of Critical Regions and Residues in the Leader Peptide, Cell, 44:451-459 (1986).

International Search Report for PCT/US11/62459, 3 pages (Apr. 11, 2012).

International Search Report for PCT/US12/41724, 5 pages (Oct. 25, 2012).

Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).

Kasuya, T. et al., In Vivo Delivery of Bionanocapsules Displaying *Phaseolus vulgaris* Agglutinin-L$_4$ Isolectin to Malignant Tumors Overexpressing *N*-Acetylglucosaminyltransferase V, Human Gene Therapy, 19:887-895 (2008).

Klibanov, A.L. et al., Amphipathic polyethyleneglycols effectively prolong the circulation time of liposomes, FEBS, 268(1): 235-237 (1990).

Kormann, M.S.D. et al., Expression of therapeutic proteins after delivery of chemically modified mRNA in mice, Nature Biotechnology, 29(2):154-157 (2011).

Kozak, M. An analysis of 5'-noncoding sequences from 699 vertebrate messenger RNAs, Nucleic Acid Research, 15(20):8125-8148 (1987).

Krieg, P.A. et al., In vitro RNA synthesis with SP6 RNA polymerase, Methods in Enzymology, 155:397-415 (1987).

Lam, J.K.W et al., Pulmonary delivery of therapeutic siRNA, Advanced Drug Delivery Reviews (2011).

Lasic, D.D. et al., Gelation of liposome interior: A novel method for drug encapsulation, FEBS, 312(2,3):255-258 (1992).

Lasic, D.D. Novel applications of liposomes, Trends in Biotechnology, 16:307-321 (1998).

Li, S. et al., In vivo gene transfer via intravenous administration of cationic lipid-protamine-DNA (LPD) complexes, Gene Therapy, 4:891-900 (1997).

Li, W. et al., Lipid-based Nanoparticles for Nucleic Acid Delivery, Pharmaceutical Research, 24(3):438-449 (2007).

Liebhaber, S.A. et al., Translation inhibition by an mRNA coding region secondary structure is determined by its proximity to the AUG initiation codon, Journal of Molecular Biology, 226(3):609-621 (1992).

Lindgren, V. et al., Human Ornithine Transcarbamylase Locus Mapped to Band Xp21.1 Near the Duchenne Muscular Dystrophy Locus, Science, 226(2675):698-700 (1984).

Liu, Y. et al., Designer Lipids Advance Systemic siRNA Delivery, Molecular Therapy, 18(4):669-670 (2010).

Love, K.T. et al., Lipid-like materials for low-dose, in vivo gene silencing, PNAS, 107(5):1864-1869 (2010).

Malone, R.W., et al., Cationic liposome-mediated RNA transfection, PNAS, 86:6077-6081 (1989).

Mansour, H.M. et al., Nanomedicine in pulmonary delivery, International Journal of Nanomedicine, 4:299-319 (2009).

Merkel, O.M. et al., Nonviral Pulmonary Delivery of siRNA, Accounts of Chemical Research, 10 pages (2011).

Monia, B.P. et al., Evaluation of 2'-Modified Oligonucleotides Containing 2'-Deoxy Gaps as Antisense Inhibitors of Gene Epression, The Journal of Biological Chemistry, 268(19):14514-14522 (1993).

Ng, J. et al., LincRNAs join the pluripotency alliance, Nature Genetics, 42:1035-1036 (2010).

Okumura, K. et al., Bax mRNA therapy using cationic liposomes for human malignant melanoma, The Journal of Gene Medicine, 10:910-917 (2008).

Probst, J. et al., Spontaneous cellular uptake of exogenous messenger RNA in vivo is nucleic acid-specific, saturable and ion dependent, Gene Therapy, 14:1175-1180 (2007).

Rabinovich, P.M. et al., Synthetic Messenger RNA as a Tool for Gene Therapy, Human Gene Therapy, 17:1027-1035 (2006).

Rejman, J. et al., Characterization and transfection properties of lipoplexes stabilized with novel exchangeable polyethylene glycol-lipid conjugates, Biochimica et Biophysica Acta, 1660:41-52 (2004).

Remington: The Science and Practice of Pharmacy, 21st Edition, Philadelphia, PA. Lippincott Williams & Wilkins (2005).

Schnierle, B.S. et al., Cap-specific mRNA (nucleoside-O2'-)-methyltransferase and poly(A) polymerase stimulatory activities of vaccinia virus are mediated by a single protein, Proceedings of the National Academy of Sciences, 89:2897-2901 (1992).

Semple, S.C. et al., Rational design of cationic lipids for siRNA delivery, Nature Biotechnology, 28(2): 172-176 (2010).

Shimada, A. et al., Translocation Pathway of the Intratracheally Instilled Ultrafine Particles from the Lung into the Blood Circulation in the Mouse, Toxicologic Pathology, 34:949-957 (2006).

Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50):47615-47622 (2001).

Suri, M. et al., Genetics for Pediatricians, Remedica Publishing, (2005).

(56) References Cited

OTHER PUBLICATIONS

Tavernier, G. et al., mRNA as gene therapeutic: How to control protein expression, Journal of Controlled Release, 150:238-247 (2011).
Van Der Gun, B.T.F et al., Serum insensitive, intranuclear protein delivery by the multipurpose cationic lipid Saint-2, Journal of Controlled Release, 123:228-238 (2007).
Van Tendeloo, V.F.I et al., mRNA-based gene transfer as a tool for gene and cell therapy, Current Opinion in Molecular Therapeutics, 9(5):423-431 (2007).
Wolf, J.A. et al., Protein/Amphipathic Polyamine Complexes Enable Highly Efficient Transfection with Minimal Toxicity, BioTechniques, 23:139-147 (1997).
Written Opinion for PCT/US10/58457, 14 pages (May 6, 2011).
Written Opinion for PCT/US11/62459, 9 pages (Apr. 11, 2012).
Written Opinion for PCT/US12/41724, 11 pages (Oct. 25, 2012).
Yamamoto, A. et al., Current prospects for mRNA gene delivery, European Journal of Pharmaceutics and Biopharmaceutics, 71:484-489 (2009).
Yokoe, H. et al., Spatial dynamics of GFP-tagged proteins investigated by local fluorescence enhancement, Nature Biotechnology, 14(10):1252-1256 (1996).
Kvasnica M., et al., "Platinum(II) complexes with steroidal esters of L-methionine and L-histidine: Synthesis, characterization and cytotoxic activity," *Bioorganic & Medicinal Chemistry* 16(7):3704-3713 (2008).
Li L., et al., "Preparation and Gene Delivery of Alkaline Amino Acids-Based Cationic Liposomes," *Arch Pharm Res* 31(7): 924-931 (2008).
Ratajczak J., et al., "Membrane-derived microvesicles: important and underappreciated mediators of cell-to-cell communication," *Leukemia* 20(9):1487-1495 (2006).
Reddy A., et al., "The Effect of Labour and Placental Separation on the Shedding of Syncytiotrophoblast Microparticles, Cell-free DNA and mRNA in Normal Pregnancy and Pre-eclampsia," *Placenta* 29(11):942-949 (2008).
Varambally S., et al., "Genomic Loss of microRNA-101 Leads to Overexpression of Histone Methyltransferase EZH2 in Cancer," *Science* 322:1695-1699 (2008).
Wiehe J., et al., "mRNA-Mediated Gene Delivery Into Human Progenitor Cells Promotes Highly Efficient Protein Expression," *Journal of Cellular and Molecular Medicine* 11(3):521-530 (2007).
International Search Report for International Application PCT/US10/58457, dated May 6, 2011.
Barreau, C. et al., Liposome-mediated RNA transfection should be used with caution, RNA, 12:1790-1793 (2006).
Cassiman, D. Gene transfer for inborn errors of metabolism of the liver: the clinical perspective, Current Pharmaceutical Design, 17(24):2550-2557 (2011).
Gonzalez-Aseguinolaza, G. et al., Gene therapy of liver diseases: A 2011 perspective, Clinics and Research in Hepatology and Gastroenterology, 35(11):699-708 (2011).
Raper, S.E. et al., Developing adenoviral-mediated in vivo gene therapy for ornithine transcarbamylase deficiency, Journal of Inherited Metabolic Disease, 21:119-137 (1998).
Chiou, H.C. et al., Enhanced resistance to nuclease degradation of nucleic acids complexed to asialoglycoprotein-polylysine carriers, Nucleic Acids Research, 22(24):5439-46 (1994).
Elton, C., The Next Next Big Thing, Boston Magazine, pp. 106-118 (Mar. 2013).
Emlen, W. et al., Effect of DNA size and strandedness on the in vivo clearance and organ localization of DNA, Clinical & Experimental Immunology, 56:185-192 (1984).
Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-92 (2004).
Harada-Shiba, M. et al., Polyion complex micelles as vectors in gene therapy—pharmacokinetics and in vivo; gene transfer, Gene Therapy, 9(6):407-14 (2002).
Kiew, L.V. et al., Effect of antisense oligodeoxynucleotides for ICAM-1 on renal ischaemia-reperfusion injury in the anaesthetised rat, The Journal of Physiology, 557(3):981-989 (2004).
Lu, D. et al., Optimization of methods to achieve mRNA-mediated transfection of tumor cells in vitro and in vivo employing cationic liposome vectors, Cancer Gene Therapy, 1(4):245-52 (1994).
Maeda-Mamiya, R. et al.,. In vivo gene delivery by cationic tetraamino; fullerene, Proceedings of National Academy of Sciences U S A, 107(12):5339-44 (2010).
Melton, D.A. et al., Efficient in vitro synthesis of biologically active RNA and RNA hybridization probes from; plasmids containing a bacteriophage SP6 promoter, Nucleic Acids Research, 12(18):7035-56 (1984).
Tagawa, M. et al., Gene expression and active virus replication in the liver after injection of duck hepatitis B virus DNA into the peripheral vein of ducklings, Journal of Hepatology, 24:328-334 (1996).
Third Party Preissuance Submission Under 37 CFR § 1.290 (Oct. 25, 2013).
Tsui, N.B. et al., Stability of endogenous and added RNA in blood specimens, serum, and plasma, Clinical Chemistry, 48(10):1647-53 (2002).
Tuschl, T. et al., Targeted mRNA degradation by double-stranded RNA in vitro, Genes and Development, 13(24):3191-7 (1999).
Ye, X. et al., Nucleic Acids, Protein Synthesis, and Molecular Genetics: Prolonged Metabolic Correction in Adult Ornithine Transcarbamylase-deficient Mice with Adenoviral Vectors, The Journal of Biological Chemistry, 271:3639-3646 (1996).

* cited by examiner

5' CMV Sequences:

UAAUACGACUCACUAUAGGACAGAUCGCCUGGAGACGCCAUCCACGCUGUUUUGACCUC
CAUAGAAGACACCGGGACCGAUCCAGCCUCCGCGGCCGGGAACGGUGCAUUGGAACGCG
GAUUCCCCGUGCCAAGAGUGACUCACCGUCCUUGACACG (SEQ ID NO: 2)

GGACAGAUCGCCUGGAGACGCCAUCCACGCUGUUUUGACCUCCAUAGAAGACACCGGGA
CCGAUCCAGCCUCCGCGGCCGGGAACGGUGCAUUGGAACGCGGAUUCCCCGUGCCAAGA
GUGACUCACCGUCCUUGACACG (SEQ ID NO: 1)

3' hGH Sequence:

CGGGUGGCAUCCCUGUGACCCCUCCCCAGUGCCUCUCCUGGCCCUGGAAGUUGCCACUC
CAGUGCCCACCAGCCUUGUCCUAAUAAAAUUAAGUUGCAUC (SEQ ID NO: 3)

SEQUENCE LISTING

<160> NUMBER OF SEQ ID NOS: 3

<210> SEQ ID NO 1
<211> LENGTH: 140
<212> TYPE: RNA
<213> ORGANISM: Artificial
<220> FEATURE:
<223> OTHER INFORMATION: CMV sequence

<400> SEQUENCE: 1
ggacagaucg ccuggagacg ccauccacgc uguuuugacc uccauagaag acaccgggac      60
cgauccagcc uccgcggccg ggaacggugc auuggaacgc ggauucccg ugccaagagu      120 gacucaccgu ccuugacacg                                                  140

<210> SEQ ID NO 2
<211> LENGTH: 157
<212> TYPE: RNA
<213> ORGANISM: Artificial
<220> FEATURE:
<223> OTHER INFORMATION: CMV sequence

<400> SEQUENCE: 2
uaauacgacu cacuauagga cagaucgccu ggagacgcca uccacgcugu uuugaccucc      60
auagaagaca ccgggaccga uccagccucc gcggccggga acggugcauu ggaacgcgga      120
uuccccgugc caagagugac ucaccguccu ugacacg                              157

<210> SEQ ID NO 3
<211> LENGTH: 100
<212> TYPE: RNA
<213> ORGANISM: Artificial
<220> FEATURE:
<223> OTHER INFORMATION: Human Growth Hormone sequence

<400> SEQUENCE: 3
cggguggcau cccugugacc ccuccccagu gccucuccug gcccuggaag uugccacucc      60
agugcccacc agccuugucc uaauaaaauu aaguugcauc                            100

MRNA FOR USE IN TREATMENT OF HUMAN GENETIC DISEASES

RELATED APPLICATIONS

The subject application claims the benefit of U.S. Provisional Application Ser. No. 61/418,389, filed Nov. 30, 2010, the entire teachings of which are incorporated herein by reference.

BACKGROUND OF THE INVENTION

Novel approaches and therapies are still needed for the treatment of protein and enzyme deficiencies, particularly strategies and therapies which overcome the challenges and limitations associated with the administration of nucleic acids and the transfection of target cells. Additional approaches which modulate or supplement the expression of a deficient protein or enzyme and thus ameliorate the underlying deficiency would be useful in the development of appropriate therapies for associated disorders.

SUMMARY OF THE INVENTION

Disclosed herein are compositions for modulating the expression of a protein in a target cell, wherein said composition comprises at least one RNA molecule and a transfer vehicle and wherein the RNA comprises at least one modification which confers stability to the RNA. In some embodiments the RNA molecule is selected from the group consisting of mRNA, miRNA, snRNA, and snoRNA. In some embodiments the RNA molecule comprises more than one modification which confers stability to the RNA molecule.

In some embodiments the RNA molecule comprises a modification of the 5' untranslated region of said RNA molecule; for example, the modification can comprise all or a partial sequence of a CMV immediate-early 1 (IE1) gene. In some embodiments the partial sequence of the CMV immediate-early 1 (IE1) gene comprises SEQ ID NO: 2 or SEQ ID NO: 1. In other embodiments the modification comprises the inclusion of a poly A tail or a Cap1 structure.

In some embodiments the RNA molecule comprises a modification of the 3' untranslated of said RNA molecule; for example, the modification can comprise the inclusion of a sequence encoding human growth hormone (hGH) (e.g., SEQ ID NO: 3).

In some embodiments the RNA encodes ornithine carbamoyltransferase, alpha galactosidase, or erythropoietin.

Also disclosed are methods of treating a subject deficient in a protein, comprising administering a composition comprising an mRNA and a transfer vehicle, wherein the mRNA encodes a functional protein corresponding to the protein which is deficient in the subject, and wherein the mRNA comprises at least one modification which confers stability to the administered mRNA. Preferably following expression of said mRNA by a target cell a functional protein is produced. In some embodiments the functional protein is secreted from said target cell. In some embodiments the mRNA encodes ornithine carbamoyltransferase, alpha galactosidase, or erythropoietin.

Also disclosed are methods of intracellular delivery of nucleic acids that are capable of correcting existing genetic defects and/or providing beneficial functions to one or more target cells. Following successful delivery to target tissues and cells, the compositions and nucleic acids of the present invention transfect that target cell and the nucleic acids (e.g., mRNA) can be translated into the gene product of interest (e.g., a functional protein or enzyme) or can otherwise modulate or regulate the presence or expression of the gene product of interest.

The compositions and methods provided herein are useful in the management and treatment of a large number of diseases, in particular diseases which result from protein and/or enzyme deficiencies. Individuals suffering from such diseases may have underlying genetic defects that lead to the compromised expression of a protein or enzyme, including, for example, the non-synthesis of the protein, the reduced synthesis of the protein, or synthesis of a protein lacking or having diminished biological activity. For example, the methods and compositions provided herein are useful for the treatment of the urea cycle metabolic disorders that occur as a result of one or more defects in the biosynthesis of enzymes involved in the urea cycle. The methods and compositions provided herein are also useful in various in vitro and in vivo applications in which the delivery of a nucleic acid (e.g., mRNA) to a target cell and transfection of that target cell are desired.

In one embodiment, the compositions provided herein may comprise a nucleic acid, a transfer vehicle and an agent to facilitate contact with, and subsequent transfection of a target cell. The nucleic acid can encode a clinically useful gene product or protein. For example, the nucleic acid may encode a functional urea cycle enzyme. In preferred embodiments, the nucleic acid is RNA, or more preferably mRNA encoding a functional protein or enzyme.

In some embodiments, compositions and methods for increasing expression of a functional protein or enzyme in a target cell are provided. For example, the compositions and methods provided herein may be used to increase the expression of a urea cycle enzyme (e.g., OTC, CPS1, ASS1, ASL or ARG1). In some embodiments, the composition comprises an mRNA and a transfer vehicle. In some embodiments, the mRNA encodes a urea cycle enzyme. In some embodiments the mRNA can comprise one or more modifications that confer stability to the mRNA (e.g., compared to a wild-type or native version of the mRNA) and/or may also comprise one or more modifications relative to the wild-type which correct a defect implicated in the associated aberrant expression of the protein. For example, the nucleic acids of the present invention may comprise modifications to one or both of the 5' and 3' untranslated regions. Such modifications may include, but are not limited to, the inclusion of all or a partial sequence of a promoter (e.g., a viral promoter sequence such as the cytomegalovirus (CMV) immediate-early 1 (IE1) gene), a poly A tail, a Cap1 structure or a sequence encoding all or a portion of human growth hormone (hGH)). Notably in this context the promoter sequence does not function as a promoter, as it is joined to an RNA sequence, e.g., an mRNA sequence rather than a DNA sequence. Such modifications may further comprise the addition of nucleic acids which attract ribosomes (e.g., by virtue of their nucleic acid composition or secondary structure).

Methods of treating a subject, wherein the subject has a protein or enzyme deficiency, are also provided. The methods can comprise administering a composition provided herein. For example, methods of treating or preventing conditions in which production of a particular protein and/or utilization of a particular protein is inadequate or compromised are provided. In one embodiment, the methods provided herein can be used to treat a subject having a deficiency in one or more urea cycle enzymes. The method can comprise contacting and transfecting target cells or tissues (such as hepatocytes that are deficient in one or more urea cycle enzymes) with a composition provided herein, wherein the nucleic acid encodes the deficient urea cycle enzyme. In this manner, the expression of the deficient enzyme in the target cell is increased, which in turn is expected to ameliorate the effects of the underlying enzyme deficiency. The protein or enzyme expressed by the target cell from the translated mRNA may be retained within the cytosol of the target cell or alternatively may be secreted extracellularly. In some embodiments, the nucleic acid is an mRNA. In some embodiments, the mRNA comprises a modification that confers stability to the mRNA (e.g., when compared to the wild-type or native version of the mRNA). For example, the mRNA encoding a functional enzyme may comprise one or more modifications to one or both of the 5' and 3' untranslated regions.

Methods of expressing a functional protein or enzyme (e.g., a urea cycle enzyme) in a target cell are also provided. In some embodiments, the target cell is deficient in the protein or enzyme, e.g., a urea cycle enzyme. The methods comprise contacting the target cell with a composition comprising an mRNA and a transfer vehicle. Following expression of the protein or enzyme encoded by the mRNA, the expressed protein or enzyme may be retained within the cytosol of the target cell or alternatively may be secreted extracellularly. In some embodiments, the mRNA encodes a urea cycle enzyme. In some embodiments the mRNA can comprise one or more modifications that confer stability to the mRNA and/or may also comprise one or more modifications relative to the wild-type that correct a defect implicated in the associated aberrant expression of the protein. In some embodiments, the compositions and methods of the present invention rely on the target cells to express the functional protein or enzyme encoded by the exogenously administered nucleic acid (e.g., mRNA). Because the protein or enzyme encoded by the exogenous mRNA are translated by the target cell, the proteins and enzymes expressed may be characterized as being less immunogenic relative to their recombinantly prepared counterparts.

Also provided are compositions and methods useful for facilitating the transfection and delivery of one or more nucleic acids (e.g., mRNA) to target cells. For example, the compositions and methods of the present invention contemplate the use of targeting ligands capable of enhancing the affinity of the composition to one or more target cells. In one embodiment, the targeting ligand is apolipoprotein-B or apolipoprotein-E and corresponding target cells express low-density lipoprotein receptors, thereby facilitating recognition of the targeting ligand. The methods and compositions of the present invention may be used to preferentially target a vast number of target cells. For example, contemplated target cells include, but are not limited to, hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

The above discussed and many other features and attendant advantages of the present invention will become better understood by reference to the following detailed description of the invention when taken in conjunction with the accompanying examples. The various embodiments described herein are complimentary and can be combined or used together in a manner understood by the skilled person in view of the teachings contained herein.

BRIEF DESCRIPTION OF THE DRAWING

FIG. 1 shows the nucleotide sequences of 5' CMV sequences (SEQ ID NO: 2 and SEQ ID NO: 1) and a 3' hGH sequence (SEQ ID NO: 3) which may, in particular embodiments, be used to flank an mRNA sequence of interest.

DETAILED DESCRIPTION OF THE INVENTION

Disclosed herein are compositions that facilitate the delivery of nucleic acids to, and the subsequent transfection of, target cells. In particular, the compositions provided herein are useful for the treatment of diseases which result from the deficient production of proteins and/or enzymes. For example, suitable diseases that may be treated are those in which a genetic mutation in a particular gene causes affected cells to not express, have reduced expression of, or to express a non-functional product of that gene. Contacting such target cells with the compositions of the present invention such that the target cells are transfected with a nucleic acid encoding a functional version of the gene product allows the production of a functional protein or enzyme product this is useful in the treatment of such deficiency. In particular embodiments, the compositions comprise one or more modifications that confer stability to the nucleic acid (e.g., mRNA) and/or comprise one or more modifications relative to the wild-type that correct a defect implicated in the associated aberrant expression of the protein.

Provided herein are compositions for modulating the expression of a protein in a target cell. In some embodiments, the composition comprises an RNA molecule and a transfer vehicle. In preferred embodiments the composition comprises an mRNA molecule comprising one or more modifications that confer stability and/or increased half-life in vivo to the mRNA and/or comprising one or more modifications relative to the wild-type that correct a defect implicated in the associated aberrant expression of the protein. In some embodiments, the mRNA of the composition can be modified to impart enhanced stability (e.g., relative to the wild-type version of the mRNA and/or the version of the mRNA found endogenously in the target cell). For example, the mRNA of the composition can include a modification compared to a wild-type version of the mRNA, wherein the modification confers stability to the mRNA of the composition.

Provided herein are methods of and compositions for modulating the level of mRNA and/or the expression of protein in a subject. In some embodiments, the compositions provided herein are capable of modulating the expression of a particular protein by increasing the level/amount of mRNA encoding that protein in a target cell or tissue. Delivery of an mRNA encoding the desired protein can be achieved as described herein, and the mRNA is translated by the target cell to produce protein. In some embodiments, the mRNA of the composition is more stable (e.g., has limited or reduced nuclease susceptibility) compared to a wild-type and/or endogenous version of the nucleic acid, as the mRNA comprises one or more modifications that confer stability and/or increased half-life in vivo to the mRNA and/or comprises one or more modifications relative to the wild-type that correct a defect implicated in an associated aberrant expression of the protein.

In other embodiments, the compositions provided herein are capable of modulating the expression of a particular protein by decreasing expression of mRNA encoding that protein in a target cell or tissue. For example, in one embodiment, the composition comprises a miRNA or a nucleic acid encoding miRNA where the miRNA is capable of reducing or eliminating expression of a particular mRNA in a target cell. In some embodiments, the nucleic acid of the composition is more stable (e.g., has limited or reduced nuclease susceptibility) compared to a wild-type and/or endogenous version of the nucleic acid.

As used herein, the term "nucleic acid" refers to genetic material (e.g., oligonucleotides or polynucleotides comprising DNA or RNA). In some embodiments, the nucleic acid of the compositions is RNA. Suitable RNA includes mRNA, siRNA, miRNA, snRNA and snoRNA. Contemplated nucleic acids also include large intergenic non-coding RNA (lincRNA), which generally do not encode proteins, but rather function, for example, in immune signaling, stem cell biology and the development of disease. (See, e.g., Guttman, et al., 458: 223-227 (2009); and Ng, et al., Nature Genetics 42: 1035-1036 (2010), the contents of which are incorporated herein by reference). In a preferred embodiment, the nucleic acids of the invention include RNA or stabilized RNA encoding a protein or enzyme. The present invention contemplates the use of such nucleic acids (and, in particular, RNA or stabilized RNA) as a therapeutic capable of facilitating the expression of a functional enzyme or protein, and preferably the expression of a functional enzyme of protein in which a subject is deficient (e.g., a urea cycle enzyme). The term "functional", as used herein to qualify a protein or enzyme, means that the protein or enzyme has biological activity, or alternatively is able to perform the same or a similar function as the native or normally-functioning protein or enzyme. The subject nucleic acid compositions of the present invention are useful for the treatment of various metabolic or genetic disorders, and in particular those genetic or metabolic disorders which involve the non-expression, misexpression or deficiency of a protein or enzyme.

In the context of the present invention the term "expression" is used in a broad sense to refer to either the transcription of a specific gene or nucleic acid into at least one mRNA transcript, or the translation of at least one mRNA or nucleic acid into a protein or enzyme. For example, contemplated by the present invention are compositions which comprise one or more mRNA nucleic acids which encode functional proteins or enzymes, and in the context of such mRNA nucleic acids, the term expression refers to the translation of such mRNA to produce the protein or enzyme encoded thereby.

The nucleic acids provided herein can be introduced into cells or tissues of interest. In some embodiments, the nucleic acid is capable of being translated (e.g., the translation of the encoded protein or enzyme from a synthetic or exogenous mRNA transcript) or otherwise capable of conferring a beneficial property to the target cells or tissues (e.g., reducing the expression of a target nucleic acid or gene). The nucleic acid may encode, for example, a hormone, enzyme, receptor, polypeptide, peptide or other protein of interest. A nucleic acid may also encode a small interfering RNA (siRNA) or antisense RNA for the purpose of decreasing or eliminating expression of an endogenous nucleic acid or gene. In one embodiment of the present invention, the nucleic acid (e.g., mRNA encoding a deficient protein or enzyme) may optionally have chemical or biological modifications which, for example, improve the stability and/or half-life of such nucleic acid or which improve or otherwise facilitate translation.

The nucleic acids of the present invention may be natural or recombinant in nature and may exert their therapeutic activity using either sense or antisense mechanisms of action.

Also contemplated by the present invention is the co-delivery of one or more unique nucleic acids to target cells, for example, by combining two unique nucleic acids into a single transfer vehicle. In one embodiment of the present invention, a therapeutic first nucleic acid, such as mRNA encoding galactose-1-phosphate uridyltransferase (GALT), and a therapeutic second nucleic acid, such as mRNA encoding galatokinase (GALK), may be formulated in a single transfer vehicle and administered (e.g., for the treatment of galactosemia). The present invention also contemplates co-delivery and/or co-administration of a therapeutic first nucleic acid and a second nucleic acid to facilitate and/or enhance the function or delivery of the therapeutic first nucleic acid. For example, such a second nucleic acid (e.g., exogenous or synthetic mRNA) may encode a membrane transporter protein that upon expression (e.g., translation of the exogenous or synthetic mRNA) facilitates the delivery or enhances the biological activity of the first nucleic acid. Alternatively, the therapeutic first nucleic acid may be administered with a second nucleic acid that functions as a "chaperone" for example, to direct the folding of either the therapeutic first nucleic acid or endogenous nucleic acids.

Also contemplated is the delivery of one or more therapeutic nucleic acids to treat a single disorder or deficiency, wherein each such therapeutic nucleic acid functions by a different mechanism of action. For example, the compositions of the present invention may comprise a therapeutic first nucleic acid which, for example, is administered to correct an endogenous protein or enzyme deficiency, and which is accompanied by a second nucleic acid, which is administered to deactivate or "knock-down" a malfunctioning endogenous nucleic acid and its protein or enzyme product. Such nucleic acids may encode, for example mRNA and siRNA.

The nucleic acids provided herein, and in particular the mRNA nucleic acids provided herein, preferably retain at least some ability to be translated, thereby producing a functional protein or enzyme within a target cell. Accordingly, the present invention relates to the administration of a stabilized nucleic acid (e.g., mRNA which has been stabilized against in vivo nuclease digestion or degradation) to modulate the expression of a gene or the translation of a functional enzyme or protein within a target cell. In a preferred embodiment of the present invention, the activity of the nucleic acid (e.g., mRNA encoding a functional protein or enzyme) is prolonged over an extended period of time. For example, the activity of the nucleic acids may be prolonged such that the compositions of the present invention are administered to a subject on a semi-weekly or bi-weekly basis, or more preferably on a monthly, bi-monthly, quarterly or an annual basis. The extended or prolonged activity of the compositions of the present invention, and in particular of the mRNA comprised therein, is directly related to the quantity of functional protein or enzyme translated from such mRNA. Similarly, the activity of the compositions of the present invention may be further extended or prolonged by modifications made to improve or enhance translation of the mRNA nucleic acids. For example, the Kozac consensus sequence plays a role in the initiation of protein translation, and the inclusion of such a Kozac consensus sequence in the mRNA nucleic acids of the present invention may further extend or prolong the activity of the mRNA nucleic acids. Furthermore, the quantity of functional protein or enzyme translated by the target cell is a function of the quantity of nucleic acid (e.g., mRNA) delivered to the target cells and the stability of such nucleic acid. To the extent that the stability of the nucleic acids of the present invention may be improved or enhanced, the half-life, the activity of the translated protein or enzyme and the dosing frequency of the composition may be further extended.

Accordingly, in a preferred embodiment, the nucleic acids provided herein comprise at least one modification which confers increased or enhanced stability to the nucleic acid, including, for example, improved resistance to nuclease digestion in vivo. As used herein, the terms "modification"

and "modified" as such terms relate to the nucleic acids provided herein, include at least one alteration which preferably enhances stability and renders the nucleic acid more stable (e.g., resistant to nuclease digestion) than the wild-type or naturally occurring version of the nucleic acid. As used herein, the terms "stable" and "stability" as such terms relate to the nucleic acids of the present invention, and particularly with respect to the mRNA, refer to increased or enhanced resistance to degradation by, for example nucleases (i.e., endonucleases or exonucleases) which are normally capable of degrading such RNA. Increased stability can include, for example, less sensitivity to hydrolysis or other destruction by endogenous enzymes (e.g., endonucleases or exonucleases) or conditions within the target cell or tissue, thereby increasing or enhancing the residence of such nucleic acids in the target cell, tissue, subject and/or cytoplasm. The stabilized nucleic acid molecules provided herein demonstrate longer half-lives relative to their naturally occurring, unmodified counterparts (e.g., the wild-type version of the nucleic acid). Also contemplated by the terms "modification" and "modified" as such terms related to the nucleic acids of the present invention are alterations which improve or enhance translation of mRNA nucleic acids, including for example, the inclusion of sequences which function in the initiation of protein translation (e.g., the Kozac consensus sequence). (Kozak, M., Nucleic Acids Res 15 (20): 8125-48 (1987)).

In some embodiments, the nucleic acids of the present invention have undergone a chemical or biological modification to render them more stable. Exemplary modifications to a nucleic acid include the depletion of a base (e.g., by deletion or by the substitution of one nucleotide for another) or modification of a base, for example, the chemical modification of a base. The phrase "chemical modifications" as used herein, includes modifications which introduce chemistries which differ from those seen in naturally occurring nucleic acids, for example, covalent modifications such as the introduction of modified nucleotides, (e.g., nucleotide analogs, or the inclusion of pendant groups which are not naturally found in such nucleic acid molecules).

In addition, suitable modifications include alterations in one or more nucleotides of a codon such that the codon encodes the same amino acid but is more stable than the codon found in the wild-type version of the nucleic acid. For example, an inverse relationship between the stability of RNA and a higher number cytidines (C's) and/or uridines (U's) residues has been demonstrated, and RNA devoid of C and U residues have been found to be stable to most RNases (Heidenreich, et al. J Biol Chem 269, 2131-8 (1994)). In some embodiments, the number of C and/or U residues in an mRNA sequence is reduced. In a another embodiment, the number of C and/or U residues is reduced by substitution of one codon encoding a particular amino acid for another codon encoding the same or a related amino acid. Contemplated modifications to the mRNA nucleic acids of the present invention also include the incorporation of pseudouridines. The incorporation of pseudouridines into the mRNA nucleic acids of the present invention may enhance stability and translational capacity, as well as diminishing immunogenicity in vivo. (See, e.g., Karikó, K., et al., Molecular Therapy 16 (11): 1833-1840 (2008)). Substitutions and modifications to the nucleic acids of the present invention may be performed by methods readily known to one or ordinary skill in the art.

The constraints on reducing the number of C and U residues in a sequence will likely be greater within the coding region of an mRNA, compared to an untranslated region, (i.e., it will likely not be possible to eliminate all of the C and U residues present in the message while still retaining the ability of the message to encode the desired amino acid sequence). The degeneracy of the genetic code, however presents an opportunity to allow the number of C and/or U residues that are present in the sequence to be reduced, while maintaining the same coding capacity (i.e., depending on which amino acid is encoded by a codon, several different possibilities for modification of RNA sequences may be possible). For example, the codons for Gly can be altered to GGA or GGG instead of GGU or GGC.

The term modification also includes, for example, the incorporation of non-nucleotide linkages or modified nucleotides into the nucleic acid sequences of the present invention (e.g., modifications to one or both the 3' and 5' ends of an mRNA molecule encoding a functional protein or enzyme). Such modifications include the addition of bases to a nucleic acid sequence (e.g., the inclusion of a poly A tail or a longer poly A tail), the alteration of the 3' UTR or the 5' UTR, complexing the nucleic acid with an agent (e.g., a protein or a complementary nucleic acid molecule), and inclusion of elements which change the structure of a nucleic acid molecule (e.g., which form secondary structures).

The poly A tail is thought to stabilize natural messengers and synthetic sense RNA. Therefore, in one embodiment a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)). In one embodiment, the length of the poly A tail is at least about 90, 200, 300, 400, or at least about 500 nucleotides. In one embodiment, the length of the poly A tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of protein expression in a cell. In one embodiment, the stabilized nucleic acid molecules are sufficiently resistant to in vivo degradation (e.g., by nucleases), such that they may be delivered to the target cell without a transfer vehicle.

In one embodiment, a nucleic acid encoding a protein can be modified by the incorporation of 3' and/or 5' untranslated (UTR) sequences which are not naturally found in the wild-type nucleic acid. In one embodiment, 3' and/or 5' flanking sequence which naturally flanks an mRNA and encodes a second, unrelated protein can be incorporated into the nucleotide sequence of an mRNA molecule encoding a therapeutic or functional protein in order to modify it. For example, 3' or 5' sequences from mRNA molecules which are stable (e.g., globin, actin, GAPDH, tubulin, histone, or citric acid cycle enzymes) can be incorporated into the 3' and/or 5' region of a sense mRNA nucleic acid molecule to increase the stability of the sense mRNA molecule.

Also contemplated by the present invention are other modifications to the nucleic acid sequences made to one or both of the 3' and 5' ends of the nucleic acid. For example, the present invention contemplates modifications to one or both of the 3' and the 5' ends of the nucleic acids (e.g., mRNA) to include at least a partial sequence of a CMV immediate-early 1 (IE1)

gene, or a fragment thereof (e.g., SEQ ID NO: 2 or SEQ ID NO: 1) to improve the nuclease resistance and/or improve the half-life of the nucleic acid. In addition to increasing the stability of the mRNA nucleic acid sequence, it has been surprisingly discovered the inclusion of a partial sequence of a CMV immediate-early 1 (1E1) gene at the 5' end enhances the translation of the mRNA and the expression of the functional protein or enzyme. Also contemplated is the inclusion of a sequence encoding human growth hormone (hGH), or a fragment thereof (e.g., SEQ ID NO: 3) to one or both of the 3' and 5' ends of the nucleic acid (e.g., mRNA) to further stabilize the nucleic acid. Generally, preferred modifications improve the stability and/or pharmacokinetic properties (e.g., half-life) of the nucleic acid relative to their unmodified counterparts, and include, for example modifications made to improve such nucleic acid's resistance to in vivo nuclease digestion.

In some embodiments, the composition can comprise a stabilizing reagent. The compositions can include one or more formulation reagents that bind directly or indirectly to, and stabilize the nucleic acid, thereby enhancing residence time in the cytoplasm of a target cell. Such reagents preferably lead to an improved half-life of a nucleic acid in the target cells. For example, the stability of an mRNA and efficiency of translation may be increased by the incorporation of "stabilizing reagents" that form complexes with the nucleic acids (e.g., mRNA) that naturally occur within a cell (see e.g., U.S. Pat. No. 5,677,124). Incorporation of a stabilizing reagent can be accomplished for example, by combining the poly A and a protein with the mRNA to be stabilized in vitro before loading or encapsulating the mRNA within a transfer vehicle. Exemplary stabilizing reagents include one or more proteins, peptides, aptamers, translational accessory protein, mRNA binding proteins, and/or translation initiation factors.

Stabilization of the compositions may also be improved by the use of opsonization-inhibiting moieties, which are typically large hydrophilic polymers that are chemically or physically bound to the transfer vehicle (e.g., by the intercalation of a lipid-soluble anchor into the membrane itself, or by binding directly to active groups of membrane lipids). These opsonization-inhibiting hydrophilic polymers form a protective surface layer which significantly decreases the uptake of the liposomes by the macrophage-monocyte system and reticulo-endothelial system (e.g., as described in U.S. Pat. No. 4,920,016, the entire disclosure of which is herein incorporated by reference). Transfer vehicles modified with opsonization-inhibition moieties thus remain in the circulation much longer than their unmodified counterparts.

When RNA is hybridized to a complementary nucleic acid molecule (e.g., DNA or RNA) it may be protected from nucleases. (Krieg, et al. Melton. Methods in Enzymology. 1987; 155, 397-415). The stability of hybridized mRNA is likely due to the inherent single strand specificity of most RNases. In some embodiments, the stabilizing reagent selected to complex a nucleic acid is a eukaryotic protein, (e.g., a mammalian protein). In yet another embodiment, the nucleic acid molecule (e.g., mRNA) for use in sense therapy can be modified by hybridization to a second nucleic acid molecule. If an entire mRNA molecule were hybridized to a complementary nucleic acid molecule translation initiation may be reduced. Thus in some embodiments the 5' untranslated region and the AUG start region of the mRNA molecule may optionally be left unhybridized. Following translation initiation, the unwinding activity of the ribosome complex can function even on high affinity duplexes so that translation can proceed. (Liebhaber. J. Mol. Biol. 1992; 226: 2-13; Monia, et al. J Biol Chem. 1993; 268: 14514-22.)

It will be understood that any of the above described methods for enhancing the stability of nucleic acids may be used either alone or in combination with one or more of any of the other above-described methods and/or compositions.

In one embodiment, the compositions of the present invention facilitate the delivery of nucleic acids to target cells. In some embodiments, facilitating delivery to target cells includes increasing the amount of nucleic acid that comes in contact with the target cells. In some embodiments, facilitating delivery to target cells includes reducing the amount of nucleic acid that comes into contact with non-target cells. In some embodiments, facilitating delivery to target cells includes allowing the transfection of at least some target cells with the nucleic acid. In some embodiments, the level of expression of the product encoded by the delivered nucleic acid is increased in target cells.

The nucleic acids of the present invention may be optionally combined with a reporter gene (e.g., upstream or downstream of the coding region of the nucleic acid) which, for example, facilitates the determination of nucleic acid delivery to the target cells or tissues. Suitable reporter genes may include, for example, Green Fluorescent Protein mRNA (GFP mRNA), *Renilla* Luciferase mRNA (Luciferase mRNA), Firefly Luciferase mRNA, or any combinations thereof. For example, GFP mRNA may be fused with a nucleic acid encoding OTC mRNA to facilitate confirmation of mRNA localization in the target cells, tissues or organs.

As used herein, the terms "transfect" or "transfection" mean the intracellular introduction of a nucleic acid into a cell, or preferably into a target cell. The introduced nucleic acid may be stably or transiently maintained in the target cell. The term "transfection efficiency" refers to the relative amount of nucleic acid up-taken by the target cell which is subject to transfection. In practice, transfection efficiency is estimated by the amount of a reporter nucleic acid product expressed by the target cells following transfection. Preferred are compositions with high transfection efficacies and in particular those compositions that minimize adverse effects which are mediated by transfection of non-target cells and tissues.

As provided herein, the compositions can include a transfer vehicle. As used herein, the term "transfer vehicle" includes any of the standard pharmaceutical carriers, diluents, excipients and the like which are generally intended for use in connection with the administration of biologically active agents, including nucleic acids. The compositions and in particular the transfer vehicles described herein are capable of delivering nucleic acids of varying sizes to their target cells or tissues. In one embodiment of the present invention, the transfer vehicles of the present invention are capable of delivering large nucleic acid sequences (e.g., nucleic acids of at least 1 kDa, 1.5 kDa, 2 kDa, 2.5 kDa, 5 kDa, 10 kDa, 12 kDa, 15 kDa, 20 kDa, 25 kDa, 30 kDa, or more). The nucleic acids can be formulated with one or more acceptable reagents, which provide a vehicle for delivering such nucleic acids to target cells. Appropriate reagents are generally selected with regards to a number of factors, which include, among other things, the biological or chemical properties of the nucleic acids (e.g., charge), the intended route of administration, the anticipated biological environment to which such nucleic acids will be exposed and the specific properties of the intended target cells. In some embodiments, transfer vehicles, such as liposomes, encapsulate the nucleic acids without compromising biological activity. In some embodiments, the transfer vehicle demonstrates preferential and/or substantial binding to a target cell relative to non-target cells. In a preferred embodiment, the transfer vehicle delivers its contents to the target cell such that the nucleic acids are delivered to the appropriate subcellular compartment, such as the cytoplasm.

In some embodiments, the transfer vehicle is a liposomal vesicle, or other means to facilitate the transfer of a nucleic acid to target cells and tissues. Suitable transfer vehicles include, but are not limited to, liposomes, nanoliposomes, ceramide-containing nanoliposomes, proteoliposomes, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), nanodendrimers, starch-based delivery systems, micelles, emulsions, niosomes, plasmids, viruses, calcium phosphate nucleotides, aptamers, peptides and other vectorial tags. Also contemplated is the use of bionanocapsules and other viral capsid proteins assemblies as a suitable transfer vehicle. (Hum. Gene Ther. 2008 September; 19(9):887-95). Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins and polyethylenimine. In addition, several reagents are commercially available to enhance transfection efficacy. Suitable examples include LIPOFECTIN (DOTMA:DOPE) (Invitrogen, Carlsbad, Calif.), LIPOFECTAMINE (DOSPA:DOPE) (Invitrogen), LIPOFECTAMINE2000. (Invitrogen), FUGENE, TRANSFECTAM (DOGS), and EFFECTENE. In one embodiment, the transfer vehicle is selected based upon its ability to facilitate the transfection of a nucleic acid to a target cell.

In one embodiment of the present invention, the transfer vehicle may be selected and/or prepared to optimize delivery of the nucleic acid to the target cell, tissue or organ. For example, if the target cell is a hepatocyte the properties of the transfer vehicle (e.g., size, charge and/or pH) may be optimized to effectively deliver such transfer vehicle to the target cell or organ, reduce immune clearance and/or promote retention in that target organ. Alternatively, if the target tissue is the central nervous system (e.g., mRNA administered for the treatment of neurodegenerative diseases may specifically target brain or spinal tissue) selection and preparation of the transfer vehicle must consider penetration of, and retention within the blood brain barrier and/or the use of alternate means of directly delivering such transfer vehicle to such target tissue. In one embodiment, the compositions of the present invention may be combined with agents that facilitate the transfer of exogenous nucleic acids (e.g., agents which disrupt or improve the permeability of the blood brain barrier and thereby enhance the transfer of exogenous mRNA to the target cells).

In certain embodiments, the compositions of the present invention may be loaded with diagnostic radionuclide, fluorescent materials or other materials that are detectable in both in vitro and in vivo applications. For example, suitable diagnostic materials for use in the present invention may include Rhodamine-dioleoylphosphatidylethanolamine (Rh—PE), Green Fluorescent Protein mRNA (GFP mRNA), *Renilla* Luciferase mRNA and Firefly Luciferase mRNA.

In some embodiments, the compositions of the present invention comprise one or more additional molecules (e.g., proteins, peptides, aptamers or oliogonucleotides) which facilitate the transfer of the nucleic acids (e.g., mRNA, miRNA, snRNA and snoRNA) from the transfer vehicle into an intracellular compartment of the target cell. In one embodiment, the additional molecule facilitates the delivery of the nucleic acids into, for example, the cytosol, the lysosome, the mitochondrion, the nucleus, the nucleolae or the proteasome of a target cell. Also included are agents that facilitate the transport of the translated protein of interest from the cytoplasm to its normal intercellular location (e.g., in the mitochondrion) to treat deficiencies in that organelle. In some embodiments, the agent is selected from the group consisting of a protein, a peptide, an aptamer, and an oligonucleotide.

In one embodiment, the compositions of the present invention facilitate a subject's endogenous production of one or more functional proteins and/or enzymes, and in particular the production of proteins and/or enzymes which demonstrate less immunogenicity relative to their recombinantly-prepared counterparts. In a preferred embodiment of the present invention, the transfer vehicles comprise nucleic acids which encode mRNA of a deficient protein or enzyme. Upon distribution of such compositions to the target tissues and the subsequent transfection of such target cells, the exogenous mRNA may be translated in vivo to produce a functional protein or enzyme encoded by the exogenously administered mRNA (e.g., a protein or enzyme in which the subject is deficient). Accordingly, the compositions of the present invention exploit a subject's ability to translate exogenously- or recombinantly-prepared mRNA to produce an endogenously-translated protein or enzyme, and thereby produce (and where applicable excrete) a functional protein or enzyme. The expressed or translated proteins or enzymes may also be characterized by the in vivo inclusion of native post-translational modifications which may often be absent in recombinantly-prepared proteins or enzymes, thereby further reducing the immunogenicity of the translated protein or enzyme.

The administration of mRNA encoding a deficient protein or enzyme avoids the need to deliver the nucleic acids to specific organelles within a target cell (e.g., mitochondria). Rather, upon transfection of a target cell and delivery of the nucleic acids to the cytoplasm of the target cell, the mRNA contents of a transfer vehicle may be translated and a functional protein or enzyme expressed.

The present invention also contemplates the discriminatory targeting of target cells and tissues by both passive and active targeting means. The phenomenon of passive targeting exploits the natural distributions patterns of a transfer vehicle in vivo without relying upon the use of additional excipients or means to enhance recognition of the transfer vehicle by target cells. For example, transfer vehicles which are subject to phagocytosis by the cells of the reticulo-endothelial system are likely to accumulate in the liver or spleen, and accordingly may provide means to passively direct the delivery of the compositions to such target cells.

Alternatively, the present invention contemplates active targeting, which involves the use of additional excipients, referred to herein as "targeting ligands" that may be bound (either covalently or non-covalently) to the transfer vehicle to encourage localization of such transfer vehicle at certain target cells or target tissues. For example, targeting may be mediated by the inclusion of one or more endogenous targeting ligands (e.g., apolipoprotein E) in or on the transfer vehicle to encourage distribution to the target cells or tissues. Recognition of the targeting ligand by the target tissues actively facilitates tissue distribution and cellular uptake of the transfer vehicle and/or its contents in the target cells and tissues (e.g., the inclusion of an apolipoprotein-E targeting ligand in or on the transfer vehicle encourages recognition and binding of the transfer vehicle to endogenous low density lipoprotein receptors expressed by hepatocytes). As provided herein, the composition can comprise a ligand capable of enhancing affinity of the composition to the target cell. These methods are well known in the art. In other some embodiments, the compositions of the present invention demonstrate improved transfection efficacies, and/or demonstrate enhanced selectivity towards target cells or tissues of interest. Contemplated therefore are compositions which comprise one or more ligands (e.g., peptides, aptamers, oligonucleotides, a vitamin or other molecules) that are capable of enhancing the affinity of the compositions and their nucleic acid contents for the target cells or tissues. Suitable ligands may optionally be bound or linked to the surface of the transfer vehicle. In some embodiments, the targeting ligand may span the surface of a transfer vehicle or be encapsulated within the transfer vehicle. Suitable ligands and are selected based upon their physical, chemical or biological properties (e.g., selective affinity and/or recognition of target cell surface markers or features.) Cell-specific target sites and their corresponding targeting ligand can vary widely. Suitable targeting ligands are selected such that the unique characteristics of a target cell are exploited, thus allowing the composition to discriminate between target and non-target cells. For example, compositions of the present invention may bear surface markers (e.g., apolipoprotein-B or apolipoprotein-E) that selectively enhance recognition of, or affinity to hepatocytes (e.g., by receptor-mediated recognition of and binding to such surface markers). Additionally, the use of galactose as a targeting ligand would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting ligands therefore facilitate recognition and uptake of the compositions of the present invention in target cells and tissues. Examples of suitable targeting ligands include one or more peptides, proteins, aptamers, vitamins and oligonucleotides.

As used herein, the term "subject" refers to any animal (e.g., a mammal), including, but not limited to, humans, non-human primates, rodents, and the like, to which the compositions and methods of the present invention are administered. Typically, the terms "subject" and "patient" are used interchangeably herein in reference to a human subject.

As used herein, the term "target cell" refers to a cell or tissue to which a composition of the invention is to be directed or targeted. In some embodiments, the target cells are deficient in a protein or enzyme of interest. For example, where it is desired to deliver a nucleic acid to a hepatocyte, the hepatocyte represents the target cell. In some embodiments, the nucleic acids and compositions of the present invention transfect the target cells on a discriminatory basis (i.e., do not transfect non-target cells). The compositions and methods of the present invention may be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Following transfection of one or more target cells by the compositions and nucleic acids of the present invention, expression of the protein encoded by such nucleic acid may be preferably stimulated and the capability of such target cells to express the protein of interest is enhanced. For example, transfection of a target cell with an OTC mRNA will allow expression of the OTC protein product following translation of the nucleic acid. The nucleic acids of the compositions and/or methods provided herein preferably encode a product (e.g., a protein, enzyme, polypeptide, peptide, functional RNA, and/or antisense molecule), and preferably encode a product whose in vivo production is desired.

The urea cycle metabolic disorders represent examples of protein and enzyme deficiencies which may be treated using the methods and compositions provided herein. Such urea cycle metabolic disorders include OTC deficiency, arginosuccinate synthetase deficiency (ASD) and argininosuccinate lyase deficiency (ALD). Therefore, in some embodiments, the nucleic acid of the methods and compositions provided herein encode an enzyme involved in the urea cycle, including, for example, ornithine transcarbamylase (OTC), carbamyl phosphate synthetase (CPS), argininosuccinate synthetase 1 (ASS1) argininosuccinate lyase (ASL), and arginase (ARG).

Five metabolic disorders which result from defects in the biosynthesis of the enzymes involved in the urea cycle have been described, and include ornithine transcarbamylase (OTC) deficiency, carbamyl phosphate synthetase (CPS) deficiency, argininosuccinate synthetase 1 (ASS1) deficiency (citrullinemia), argininosuccinate lyase (ASL) deficiency and arginase deficiency (ARG). Of these five metabolic disorders, OTC deficiency represents the most common, occurring in an estimated one out of every 80,000 births.

OTC is a homotrimeric mitochondrial enzyme which is expressed almost exclusively in the liver and which encodes a precursor OTC protein that is cleaved in two steps upon incorporation into the mitchondrial matrix. (Horwich A L., et al. Cell 1986; 44: 451-459). OTC deficiency is a genetic disorder which results in a mutated and biologically inactive form of the enzyme ornithine transcarbamylase. OTC deficiency often becomes evident in the first few days of life, typically after protein ingestion. In the classic severe form of OTC deficiency, within the first days of life patients present with lethargy, convulsions, coma and severe hyperammonemia, which quickly leads to a deteriorating and fatal outcome absent appropriate medical intervention. (Monish S., et al., Genetics for Pediatricians; Remedica, Cold Spring Harbor Laboratory (2005)). If improperly treated or if left untreated, complications from OTC deficiency may include developmental delay and mental retardation. OTC deficient subjects may also present with progressive liver damage, skin lesions, and brittle hair. In some affected individuals, signs and symptoms of OTC deficiency may be less severe, and may not appear until later in life.

The OTC gene, which is located on the short arm of the X chromosome within band Xp21.1, spans more than 85 kb and is comprised of 10 exons encoding a protein of 1062 amino acids. (Lindgren V., et al. Science 1984; 226: 698-7700; Horwich, A L., et al. Science 224: 1068-1074, 1984; Horwich, A L. et al., Cell 44: 451-459, 1986; Hata, A., et al., J. Biochem. 100: 717-725, 1986, which are incorporated herein by reference). The OTC enzyme catalyzes the conversion or ornithine and carbamoyl phosphate to citrulline. Since OTC is on the X chromosome, females are primarily carriers while males with nonconservative mutations rarely survive past 72 hours of birth.

In healthy subjects, OTC is expressed almost exclusively in hepatocellular mitochondria. Although not expressed in the brain of healthy subjects, OTC deficiency can lead to neurological disorders. For example, one of the usual symptoms of OTC deficiency, which is heterogeneous in its presentation, is hyperammonaemic coma (Gordon, N., Eur J Paediatr Neurol 2003;7:115-121.).

OTC deficiency is very heterogeneous, with over 200 unique mutations reported and large deletions that account for approximately 10-15% of all mutations, while the remainder generally comprises missense point mutations with smaller numbers of nonsense, splice-site and small deletion mutations. (Monish A., et al.) The phenotype of OTC deficiency is extremely heterogeneous, which can range from acute neonatal hyperammonemic coma to asymptomatic hemizygous adults. (Gordon N. Eur J Paediatr Neurol 2003; 7: 115-121). Those mutations that result in severe and life threatening neonatal disease are clustered in important structural and functional domains in the interior of the protein at sites of enzyme activity or at the interchain surface, while mutations associated with late-onset disease are located on the protein surface (Monish A., et al.) Patients with milder or partial forms of OTC deficiency may have onset of disease later in life, which may present as recurrent vomiting, neurobehavioral changes or seizures associated with hyperammonemia.

The compositions and methods of the present invention are broadly applicable to the delivery of nucleic acids, and in particular mRNA, to treat a number of disorders. In particular, the compositions and methods of the present invention are suitable for the treatment of diseases or disorders relating to the deficiency of proteins and/or enzymes. In one embodiment, the nucleic acids of the present invention encode functional proteins or enzymes that are excreted or secreted by the target cell into the surrounding extracellular fluid (e.g., mRNA encoding hormones and neurotransmitters). Alternatively, in another embodiment, the nucleic acids of the present invention encode functional proteins or enzymes that remain in the cytosol of the target cell (e.g., mRNA encoding urea cycle metabolic disorders).

Other disorders for which the present invention can be useful as a therapeutic intervention include enzyme and protein deficiencies, such as lysosomal storage diseases. Specific disorders for which the present invention can be useful as a therapeutic intervention include disorders such as SMN1-related spinal muscular atrophy (SMA); amyotrophic lateral sclerosis (ALS); GALT-related galactosemia; Cystic Fibrosis (CF); SLC3A1-related disorders including cystinuria; COL4A5-related disorders including Alport syndrome; galactocerebrosidase deficiencies; X-linked adrenoleukodystrophy and adrenomyeloneuropathy; Friedreich's ataxia; Pelizaeus-Merzbacher disease; TSC1 and TSC2-related tuberous sclerosis; Sanfilippo B syndrome (MPS IIIB); CTNS-related cystinosis; the FMR1-related disorders which include Fragile X syndrome, Fragile X-Associated Tremor/Ataxia Syndrome and Fragile X Premature Ovarian Failure Syndrome; Prader-Willi syndrome; hereditary hemorrhagic telangiectasia (AT); Niemann-Pick disease Type C1; the neuronal ceroid lipofuscinoses-related diseases including Juvenile Neuronal Ceroid Lipofuscinosis (JNCL), Juvenile Batten disease, Santavuori-Haltia disease, Jansky-Bielschowsky disease, and PTT-1 and TPP1 deficiencies; EIF2B1, EIF2B2, EIF2B3, EIF2B4 and EIF2B5-related childhood ataxia with central nervous system hypomyelination/vanishing white matter; CACNA1A and CACNB4-related Episodic Ataxia Type 2; the MECP2-related disorders including Classic Rett Syndrome, MECP2-related Severe Neonatal Encephalopathy and PPM-X Syndrome; CDKL5-related Atypical Rett Syndrome; Kennedy's disease (SBMA); Notch-3 related cerebral autosomal dominant arteriopathy with subcortical infarcts and leukoencephalopathy (CADASIL); SCN1A and SCN1B-related seizure disorders; the Polymerase G-related disorders which include Alpers-Huttenlocher syndrome, POLG-related sensory ataxic neuropathy, dysarthria, and ophthalmoparesis, and autosomal dominant and recessive progressive external ophthalmoplegia with mitochondrial DNA deletions; X-Linked adrenal hypoplasia; X-linked agammaglobulinemia; Fabry disease; and Wilson's disease.

In one embodiment, the nucleic acids, and in particular mRNA, of the present invention may encode functional proteins or enzymes. For example, the compositions of the present invention may include mRNA encoding erythropoietin (EPO), α1-antitrypsin, carboxypeptidase N, alpha galactosidase (GLA), ornithine carbamoyltransferase (OTC), or human growth hormone (hGH).

Alternatively the nucleic acids may encode full length antibodies or smaller antibodies (e.g., both heavy and light chains) to confer immunity to a subject. While one embodiment of the present invention relates to methods and compositions useful for conferring immunity to a subject (e.g., via the translation of mRNA nucleic acids encoding functional antibodies), the inventions disclosed herein and contemplated hereby are broadly applicable. In an alternative embodiment the compositions of the present invention encode antibodies that may be used to transiently or chronically effect a functional response in subjects. For example, the mRNA nucleic acids of the present invention may encode a functional monoclonal or polyclonal antibody, which upon translation (and as applicable, systemic excretion from the target cells) may be useful for targeting and/or inactivating a biological target (e.g., a stimulatory cytokine such as tumor necrosis factor). Similarly, the mRNA nucleic acids of the present invention may encode, for example, functional anti-nephritic factor antibodies useful for the treatment of membranoproliferative glomerulonephritis type II or acute hemolytic uremic syndrome, or alternatively may encode anti-vascular endothelial growth factor (VEGF) antibodies useful for the treatment of VEGF-mediated diseases, such as cancer.

The compositions of the present invention can be administered to a subject. In some embodiments, the composition is formulated in combination with one or more additional nucleic acids, carriers, targeting ligands or stabilizing reagents, or in pharmacological compositions where it is mixed with suitable excipients. For example, in one embodiment, the compositions of the present invention may be prepared to deliver nucleic acids (e.g., mRNA) encoding two or more distinct proteins or enzymes. Alternatively, the compositions of the present invention may be prepared to deliver a single nucleic acid and two or more populations or such compositions may be combined in a single dosage form or co-administered to a subject. Techniques for formulation and administration of drugs may be found in "Remington's Pharmaceutical Sciences," Mack Publishing Co., Easton, Pa., latest edition.

A wide range of molecules that can exert pharmaceutical or therapeutic effects can be delivered into target cells using compositions and methods of the present invention. The molecules can be organic or inorganic. Organic molecules can be peptides, proteins, carbohydrates, lipids, sterols, nucleic acids (including peptide nucleic acids), or any combination thereof. A formulation for delivery into target cells can comprise more than one type of molecule, for example, two different nucleotide sequences, or a protein, an enzyme or a steroid.

The compositions of the present invention may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient expression of the nucleic acid in the target cell.

Suitable routes of administration include, for example, oral, rectal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternately, the compositions of the present invention may be administered in a local rather than systemic manner, for example, via injection of the pharmaceutical composition directly into a targeted tissue, preferably in a depot or sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing compositions of the present invention complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

In one embodiment, the compositions of the present invention are formulated such that they are suitable for extended-release of the nucleic acids contained therein. Such extended-release compositions may be conveniently administered to a subject at extended dosing intervals. For example, in one embodiment, the compositions of the present invention are administered to a subject twice day, daily or every other day. In a preferred embodiment, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and liposomal vehicles which are formulated for depot administration (e.g., intramuscularly, subcutaneously, intravitreally) to either deliver or release a nucleic acids (e.g., mRNA) over extended periods of time. Preferably, the extended-release means employed are combined with modifications made to the nucleic acid to enhance stability.

While certain compounds, compositions and methods of the present invention have been described with specificity in accordance with certain embodiments, the following examples serve only to illustrate the compounds of the invention and are not intended to limit the same. Each of the publications, reference materials, accession numbers and the like referenced herein to describe the background of the invention and to provide additional detail regarding its practice are hereby incorporated by reference in their entirety.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

What is claimed is:

1. A composition for delivery of mRNA for protein expression in a target cell, comprising at least one mRNA molecule comprising a sequence encoding a protein of interest and a 5' untranslated region (UTR) comprising SEQ ID NO: 1, wherein SEQ ID NO: 1 enhances the expression of the protein of interest.

2. The composition of claim 1, wherein said mRNA molecule further comprises a poly A tail.

3. The composition of claim 1, wherein said mRNA molecule further comprises a Cap1 structure.

4. The composition of claim 1, wherein said mRNA molecule further comprises a 3' untranslated region (UTR).

5. The composition of claim 4, wherein said 3' UTR comprises a sequence encoding human growth hormone (hGH).

6. The composition of claim 5, wherein said sequence encoding human growth hormone (hGH) comprises SEQ ID NO: 3.

7. The composition of claim 1, wherein the protein of interest is ornithine carbamoyltransferase.

8. The composition of claim 1, wherein the protein of interest is alpha galactosidase.

9. The composition of claim 1, wherein the protein of interest is erythropoietin.

10. The composition of claim 1, wherein the target cell is selected from hepatocytes, epithelial cells, hematopoietic cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes or tumor cells.

11. The composition of claim 1, wherein the mRNA molecule comprises one or more nucleotide substitutions or modifications that enhance stability, translational capacity or diminish immunogenicity.

12. The composition of claim 11, wherein the one or more nucleotide substitutions or modifications include the incorporation of pseudouridine.

13. The composition of claim 1, wherein the composition further comprises a transfer vehicle.

14. The composition of claim 13, wherein the transfer vehicle is a liposomal vesicle.

* * * * *